(12) United States Patent
Degenhardt et al.

(10) Patent No.: US 9,316,752 B2
(45) Date of Patent: Apr. 19, 2016

(54) PRECLINICAL TIME OF FLIGHT IMAGING (75) Inventors: Carsten Degenhardt, Aachen (DE); Andrew Buckler, Wenham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1697 days.

(21) Appl. No.: 12/675,979

(22) PCT Filed: Aug. 26, 2008

(86) PCT No.: PCT/IB2008/053438
§ 371 (c)(1),
(2), (4) Date: Mar. 2, 2010

(87) PCT Pub. No.: WO2009/040690
PCT Pub. Date: Apr. 2, 2009

(65) Prior Publication Data
US 2010/0172565 A1 Jul. 8, 2010

Related U.S. Application Data

(60) Provisional application No. 60/974,585, filed on Sep. 24, 2007.

(51) Int. Cl.
*G06K 9/00* (2006.01)
*G01T 1/164* (2006.01)
*G01T 1/29* (2006.01)
*A61B 6/00* (2006.01)
*A61B 6/03* (2006.01)
*G01R 33/48* (2006.01)

(52) U.S. Cl.
CPC ............... *G01T 1/2985* (2013.01); *A61B 6/037* (2013.01); *A61B 6/508* (2013.01); *G01R 33/481* (2013.01)

(58) Field of Classification Search
CPC ............................... G06T 5/00; G06T 11/003
See application file for complete search history.

(56) References Cited

U.S. PATENT DOCUMENTS 4,559,597 A * 12/1985 Mullani ...................... 600/407
6,421,551 B1 7/2002 Kuth et al.
7,723,694 B2 * 5/2010 Frach et al. ............. 250/370.11
(Continued)

FOREIGN PATENT DOCUMENTS

JP 02206789 A 8/1990
WO 0234136 A2 5/2002
(Continued)

*Primary Examiner* — Robert Sorey
*Assistant Examiner* — Kristine Rapillo (57) ABSTRACT

A preclinical positron emission tomography (PET) imaging method includes acquiring time-of-flight localized PET imaging data from one or more non-human animal subjects and reconstructing the acquired data to form an image. In an illustrative PET scanner includes: radiation detectors (12) viewing an examination region; a subject support assembly (14) supporting a plurality of preclinical subjects in the examination region for simultaneous PET imaging; coincidence electronics (20) acquiring time-of-flight localized PET imaging data from the preclinical subjects using the radiation detectors; and reconstruction electronics (22) that (i) perform a filtering operation based at least in part on the time-of flight information, the filtering operation including at least one of discarding non-probative time-of-flight localized PET imaging data and associating time-of-flight localized PET imaging data with individual preclinical subjects and (ii) reconstruct the filtered data to form images of the preclinical subjects.

13 Claims, 5 Drawing Sheets

(56) References Cited

U.S. PATENT DOCUMENTS

| | | | |
|---|---|---|---|
| 7,897,926 B2* | 3/2011 | Vandenberghe | 250/363.04 |
| 8,229,200 B2* | 7/2012 | Piacsek et al. | 382/131 |
| 2004/0225214 A1* | 11/2004 | Trotter et al. | 600/436 |
| 2005/0109943 A1 | 5/2005 | Vaquero et al. | |
| 2007/0018107 A1* | 1/2007 | Fukuda et al. | 250/361 R |
| 2007/0029491 A1 | 2/2007 | Olden et al. | |
| 2009/0065699 A1* | 3/2009 | Vaquero et al. | 250/363.03 |
| 2009/0124907 A1* | 5/2009 | Bruce et al. | 600/458 |
| 2010/0166274 A1* | 7/2010 | Busch et al. | 382/131 |
| 2010/0272335 A1* | 10/2010 | Hu | G06K 9/00362 382/131 |

FOREIGN PATENT DOCUMENTS

| | | |
|---|---|---|
| WO | 2006067663 A1 | 6/2006 |
| WO | 2006111869 A2 | 10/2006 |
| WO | 2006111883 A2 | 10/2006 |

* cited by examiner

PRECLINICAL TIME OF FLIGHT IMAGING

CROSS REFERENCE TO RELATED APPLICATIONS

This application claims the benefit of U.S. provisional application Ser. No. 60/974,585 filed Sep. 24, 2007, which is incorporated herein by reference.

The following relates to the medical arts, and more particularly to preclinical imaging using positron emission tomography (PET), and is described with particular reference thereto. However, the following will find further application in other tasks such as PET imaging for veterinary diagnosis.

In conventional PET imaging, a radiopharmaceutical is administered to a subject so as to distribute through the subject or to aggregate in portions of the subject that are of interest, such as anatomical tissue of interest. The radiopharmaceutical exhibits positron-electron annihilation events that generate oppositely directed gamma rays each having energy of 511 keV. Radiation detectors arranged around the subject detect substantially simultaneous gamma ray detections, i.e. within a selected coincidence time window, and the substantially simultaneous gamma ray detections are assumed to be sourced by the same positron-electron annihilation event lying at some point along the line-of-response connecting the two substantially simultaneous or coincident gamma ray detection events. A data set of such lines-of-response is generated, and is reconstructed using filtered backprojection, iterative backprojection, or another technique to obtain an image of the radiopharmaceutical distribution in the subject.

Time of flight PET imaging is similar, but makes use of the finite time difference between the substantially coincident gamma ray detection events to localize the positron-electron annihilation event along the line-of-response. A gamma ray travels at the speed of light (c), i.e. about 3 centimeters every 100 picoseconds. The spatial localization ($\Delta x$) is given by $\Delta x \sim c \cdot \Delta t/2$, so for a radiation detector having, as a typical example, a temporal resolution of about 600 picoseconds it follows that the time-of-flight localization provides a spatial resolution along the line-of-response of about 9 centimeters. In practice, this localization may be represented, for example, by a Gaussian distribution having a FWHM of about 9 centimeters. Spatial localization on the order of $\Delta x=9$ centimeters is advantageous for imaging a typical human subject having a size substantially larger than this spatial localization.

On the other hand, a mouse, rat, guinea pig, or other small animal of the type typically used in preclinical research is of a size smaller than or comparable with the spatial localization $\Delta x$ provided by time-of-flight information. Accordingly, time-of-flight localization does not provide additional useful information as to the location of the positron-electron annihilation event within the animal. This recognition, coupled with the substantial additional expense of including high-speed radiation detectors and high-speed and high-capacity time-of-flight localization processing, has heretofore motivated against including time-of-flight capability in preclinical PET scanners.

Moreover, existing preclinical studies have typically used preclinical PET imaging to assess large-scale anatomical features of tumors or other large-scale growths resulting from cancer or other pathologies under study. For example, a study may quantify the effect of a therapy by the reduction in average tumor size (if any) in a statistically significant number of test animals. Such assessments are readily performed using PET imaging since the tumors of interest are substantially larger than the spatial resolution of a typical PET scanner. If the therapy successfully reduces the tumor size below the resolution of the conventional preclinical PET scanner, it is generally assumed that the therapy is indeed effective. This approach is convenient and provides readily comprehended metrics such as tumor size. However, the measured large-scale anatomical features may, or may not, be probative of outcome determinating aspects of the cancer such as the extent of metastasis, that is, the extent to which cancerous tissue has spread away from the primary tumor. It is known that most cancer patients succumb to the effects of metastatic cancer.

The following provides new and improved apparatuses and methods which overcome the above-referenced problems and others.

In accordance with one aspect, a preclinical positron emission tomography (PET) scanner is disclosed, comprising: radiation detectors arranged to view an examination region; coincidence electronics configured to acquire time-of-flight localized PET imaging data using the radiation detectors; and reconstruction electronics configured to reconstruct the time-of-flight localized PET imaging data to form an image representative of a distribution of a radiopharmaceutical in a preclinical subject disposed in the examination region.

In accordance with another aspect, a preclinical positron emission tomography (PET) imaging method is disclosed, comprising: acquiring time-of-flight localized PET imaging data from one or more non-human animal subjects that have been administered a radiopharmaceutical; and reconstructing the acquired time-of-flight localized PET imaging data to form an image representative of a distribution of radiopharmaceutical in a selected one or more of the non human animal subjects.

In accordance with another aspect, a preclinical positron emission tomography (PET) scanner is disclosed, comprising: radiation detectors arranged to view an examination region; a subject support assembly configured to support a plurality of preclinical subjects in the examination region for simultaneous PET imaging; coincidence electronics configured to acquire time-of-flight localized PET imaging data from the plurality of preclinical subjects using the radiation detectors; and reconstruction electronics configured to (i) perform a filtering operation based at least in part on the time-of flight information, the filtering operation including at least one of discarding non-probative time-of-flight localized PET imaging data and associating time-of-flight localized PET imaging data with individual preclinical subjects of the plurality of preclinical subjects and (ii) reconstruct the filtered time-of-flight localized PET imaging data to form images representative of radiopharmaceutical distribution in the plurality of preclinical subjects.

In accordance with another aspect, a method of assessing metastatic cancer is disclosed, comprising: acquiring time of flight localized PET imaging data of a cancer subject; reconstructing the time of flight localized PET imaging data to generate an image of a portion of the cancer subject; and computing a metastatic cancer measure quantifying distributed cancerous tissue in the imaged portion.

One advantage resides in improved preclinical imaging throughput.

Another advantage resides in improved preclinical imaging quality.

Another advantage resides in improved preclinical imaging flexibility.

Still further advantages of the present invention will be appreciated to those of ordinary skill in the art upon reading and understand the following detailed description.

The drawings are only for purposes of illustrating the preferred embodiments, and are not to be construed as limiting the invention.

Figure 1:
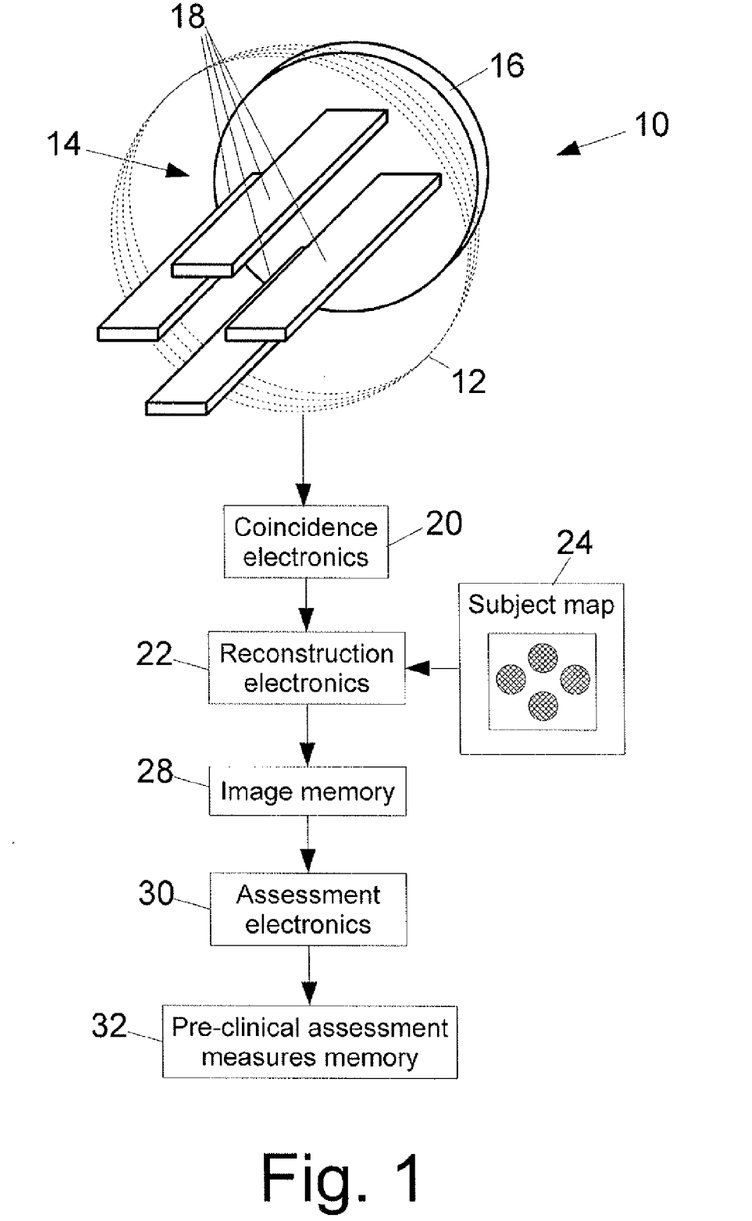
FIG. 1 diagrammatically shows a preclinical imaging system.

With reference to FIG. 1, an imaging system includes a positron emission tomography (PET) scanner 10, including one or more radiation detector rings 12 configured to detect 511 keV gamma rays emitted by positron-electron annihilation events. The detectors of the detector rings 12 are high-speed detectors having sub-nanosecond (i.e., less than one nanosecond) temporal resolution, and more preferably temporal resolution at or below about 800 picoseconds, and more preferably temporal resolution at or below about 600 picoseconds, and more preferably temporal resolution at or below about 500 picoseconds, and more preferably temporal resolution at or below about 400 picoseconds, and more preferably temporal resolution at or below about 300 picoseconds, while still faster detectors are also contemplated. Some suitable detectors include scintillators that produce light scintillations responsive to impingement of 511 keV gamma rays coupled with high-speed light detectors such as photomultiplier tube (PMT) detectors, silicon photomultiplier (SiPM) detectors, other solid state photodetectors, and so forth. Some suitable detectors are described, for example, in WO 2006/111883 A2 published Oct. 26, 2006 and in WO 2006111869 A2 published Oct. 26, 2006.

A subject support assembly 14 includes a base 16 with one or more support elements, e.g. four elongate support elements 18, to support up to four preclinical subjects, such as one or more mice, one or more rats, one or more guinea pigs, or one or more rodents of another type, or one or more rabbits, or other non-human animal subjects such as monkeys or other primates. In a given preclinical imaging session, one, two, three, or all four of the elongate support elements 18 may be occupied by preclinical subjects. Although not shown, a housing typically surrounds the one or more radiation detector rings 12, to which housing the base 16 is secured with the elongate support elements 18 projecting into the one or more radiation detector rings 12 so as to be viewed over a 360° circumferential angular span by the radiation detectors of the one or more radiation detector rings 12. Alternatively, the subject support assembly 14 can be supported separately from the housing. The elongate support elements 18 are preferably made of a material substantially transparent to gamma rays, such as a plastic or carbon fiber-based material. Although the illustrated elongate support elements 18 are shown as flat platforms, other contemplated elongate support elements include hollow tubular supports or so forth, and moreover depending upon the geometry of the preclinical subjects it is contemplated for the supports to be more or less elongated or, in some contemplated embodiments, to have no elongation. Although four elongate support elements 18 are shown in FIG. 1, it will be appreciated that the number of elongate support elements 18 can be two, three, four, five, six, or more elongate support elements, with the one or more radiation detector rings 12 sized to receive the two, three, illustrated four, five, six, or more elongate support element 18. In some embodiments, the support elements may be interlinked to define a grid having openings for receiving the preclinical subjects. In some contemplated embodiments, the PET scanner 10 is a human-sized PET scanner, and may be a commercial clinical or diagnostic PET scanner. In addition to the housing which is not illustrated, the PET scanner 10 can include other elements, components, or features not illustrated in FIG. 1, such as radiation shielding. In some contemplated embodiments, the PET scanner 10 may be a component of a hybrid imaging system such as a hybrid PET/magnetic resonance (PET/MR) imaging system, or a hybrid PET/computed tomography (PET/CT) imaging system.

With continuing reference to FIG. 1, coincidence electronics 20 recognize gamma particle detection events that are substantially simultaneous, for example as defined by a temporal coincidence time window, and that involve gamma particles at energies of about 511 keV, for example as defined by an integrated intensity window centered at about 511 keV. The coincidence electronics 20 also include a time-of-flight localization component that makes use of the sub-nanosecond speed of the radiation detectors of the one or more radiation detector rings 20 to localize the sourcing electron-positron annihilation event along a line-of-response connecting the two substantially coincident gamma particle detection events. For example, in some embodiments the time-of-flight localization is represented as a Gaussian or other statistical probability distribution having its abscissa along the line-of-response. The coincidence electronics 20 can be partially or wholly integrated into the one or more radiation detector rings 20, or can be partially or wholly separate electronics components.

In a typical preclinical imaging session, preclinical subjects are administered a radiopharmaceutical that aggregates in an organ or tissue related to the pathology under study, or in cancerous or other abnormal tissue related to the pathology under study. The preclinical subjects are secured on or in the support elements 18, anaesthesia is optionally administered to the preclinical subjects before or after securing onto or in the support elements 18, and the subject support assembly 14 with the secured preclinical subjects is inserted into the PET scanner 10. Imaging data in the form of time-of-flight localized lines-of-response are acquired by the one or more radiation detector rings 12 and the coincidence electronics 20.

The acquired data are reconstructed by reconstruction electronics 22, which may comprise a suitably programmed computer, microprocessor, or microcontroller, digital, analog, or mixed application-specific integrated circuitry (ASIC), or so forth. The reconstruction generates an image representative of the distribution of radiopharmaceutical in one or more of the preclinical subjects. It is to be understood that terms such as "subject image" or "image" as used herein denote images generated by reconstruction that are representative of the distribution of radiopharmaceutical in the preclinical subject or subjects, possibly also including features or artifacts such as shadowing due to gamma ray absorptive material in the preclinical subject or elsewhere in the examination region, artifacts introduced by the reconstruction algorithm or other processing, and so forth.

The reconstruction electronics 22 employ a suitable reconstruction algorithm such as filtered backprojection, an iterative reconstruction algorithm, or so forth, with the time-of-flight localization information optionally taken into account. The reconstruction electronics 22 optionally further employ a subject map 24 that identifies the locations of the preclinical subjects, so as to enable the reconstruction electronics 22 to discard time-of-flight localized lines-of-response that are not probative of any of the preclinical subjects, for example because they are random noise events or have been scattered en route to the detector, and to optionally associate time-of-flight localized lines-of-response with sourcing preclinical subjects. When the subject map 24 is known a priori, the subject map 24 can optionally be used to refine the time of flight localization.

In some embodiments, the subject map 24 comprises stored data generated based on a priori knowledge of the geometry of the PET scanner 10 and the subject support assembly 14, optionally further taking into account a priori knowledge as to which of the support elements 18 are loaded with preclinical subjects. In such embodiments, the subject map 24 is typically approximate, for example defining circular or otherwise-shaped container regions in which individual preclinical subjects are disposed but not delineating the perimeters of the preclinical subjects.

In some embodiments, the subject map 24 is generated from an initial reconstruction of the acquired imaging data— for example, a two-pass approach can be used in which an initial pass provides the subject map 24 and a subsequent pass makes use of the subject map 24 to refine or improve the reconstruction. In these embodiments, the subject map 24 can be relatively more precise, such as providing an approximate delineation of the perimeters of the preclinical subjects, or of the perimeters of an organ of interest in the preclinical subjects. Alternatively, the subject map derived from the first-pass reconstruction can be approximate, for example defining container circles, ovals, rectangles, or the like large enough to encompass the corresponding subject images. In another approach, a computed tomography (CT) or magnetic resonance (MR) image is used to define containers or other delineation of subjects.

The subject map 24 can also be used to segment the resulting reconstructed image, that is, to identify portions of the reconstructed image corresponding to each preclinical subject. For example, if the four illustrated subject supports 18 each support a preclinical subject, then the resulting reconstructed image is suitably divided into four images, one for each subject. The resulting image or images are stored in an image memory 28. Assessment electronics 30, which may comprise a suitably programmed computer, microprocessor, or microcontroller, digital, analog, or mixed ASIC, or so forth, process the image to generate quantitive preclinical study results, such as an average tumor size for each preclinical subject.

Because of the high image quality achievable due to the time-of-flight localization and optional data filtering performed in conjunction with the subject map 24, in some embodiments relating to cancer treatment or therapy the assessment electronics 30 are configured to compute one or more metastatic cancer measures that quantify the spread of cancerous tissue from the primary or nucleation site. For example, the assessment electronics 30 may compute a density of threaded or distributed cancerous tissue in a portion of the subject into which the metastatic cancer has spread. Such a metastatic cancer density parameter can be computed, for example, as a ratio of the count of pixels or voxels identified as belonging to cancerous tissue (based, for example, on having intensity values lying in a range attributable to cancerous tissue) respective to a count of pixels or voxels identified as belonging to benign tissue. The pre-clinical assessment electronics 30 in some embodiments classifies pixels or voxels of each preclinical subject image as one of cancerous or non-cancerous and generates the metastatic cancer measure based at least on a count or spatial distribution of the cancerous pixels or voxels. A preclinical assessment measures memory 32 stores the assessment measure or measures computed by the assessment electronics 30.

Figure 2:
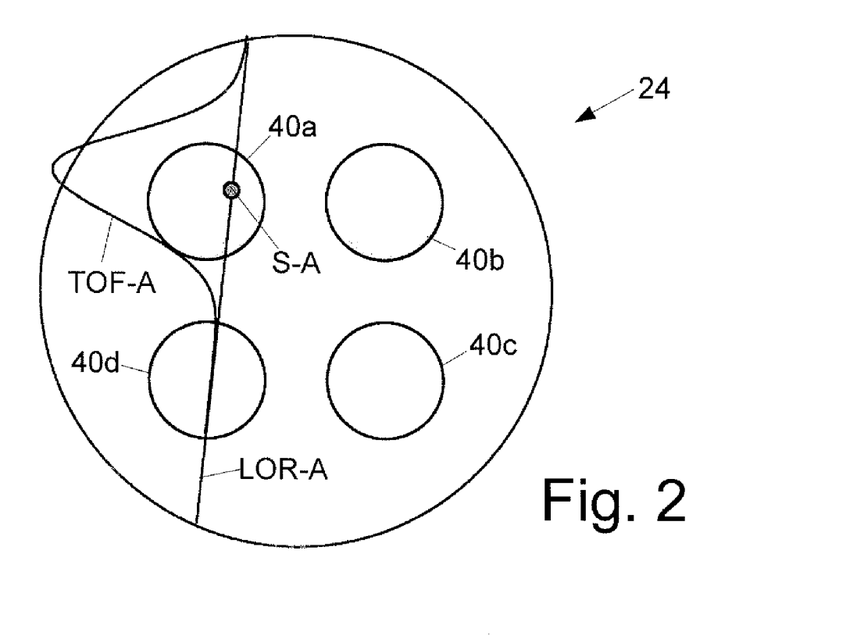
FIG. 2 diagrammatically shows association of a PET line-of-response to one of four simultaneously imaged preclinical subjects based in part on time-of-flight localization.

With reference to FIG. 2, an illustrative example is provided of using the subject map 24 to associate a time-of-flight localized line-of-response with a particular preclinical subject. The illustrative subject map 24 of FIG. 2 includes four circular container regions 40a, 40b, 40c, 40d corresponding to four preclinical subjects on the four subject support elements 18. It is noted in passing that if, for example, the subject support corresponding to the container region 40b (for example) is empty, then the corresponding container 40b is suitably omitted from the subject map 24.

In FIG. 2, a line-of-response LOR-A passes through two different container regions, namely container regions 40a, 40d. Thus, based only on the line-of-response without taking into account time-of-flight localization information, it is not possible to determine whether LOR-A was sourced by the preclinical subject corresponding to container region 40a or by the preclinical subject corresponding to container region 40d. FIG. 2 also shows the time-of-flight localization information represented as a Gaussian distribution TOF-A. In the graphical representation shown in FIG. 2, the distance of any point along the Gaussian distribution TOF-A to the line-of-response LOR-A, which serves as the abscissa for the Gaussian distribution graphical representation, is indicative of the probability that the sourcing electron-positron annihilation event is at that position along the line-of-response LOR-A. The time-of-flight information TOF-A indicates a much higher probability that the line-of-response LOR-A originated in the preclinical subject corresponding to the container region 40a as compared with a much lower probability that the line-of-response LOR-A originated in the preclinical subject corresponding to the container region 40d. A point S-A labeled in FIG. 2 indicates the most likely position of the sourcing electron-positron annihilation event for the line-of-response LOR-A.

In the illustrative example of FIG. 2, the time-of-flight localization has a resolution comparable to the size of one of the container regions 40a, 40b, 40c, 40d, and hence has a size comparable to or larger than the preclinical subjects being imaged. Heretofore, under such a configuration the art has viewed time-of-flight localization as being of little value. However, as shown in FIG. 2, time of flight localization can be usefully employed to associate the line-of-response LOR-A with a particular preclinical subject, namely the subject corresponding to the container region 40a in the illustrative example of FIG. 2, which in turn can optionally be used to refine the localization.

Figure 3:
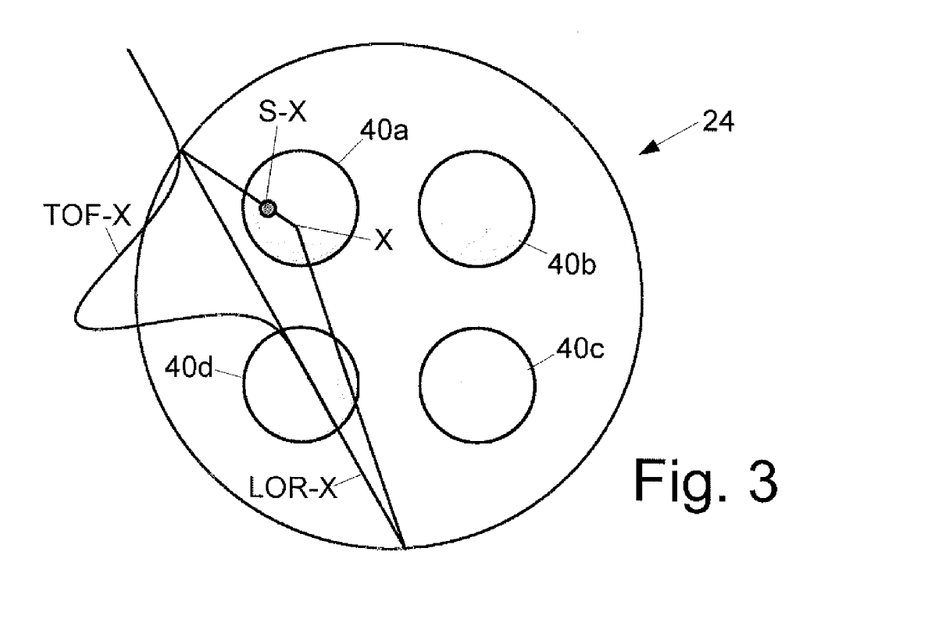
FIG. 3 diagrammatically shows identification of a scattered event, the identification based in part on time-of-flight localization resulting in a PET line-of-response associated with none of four simultaneously imaged preclinical subjects.

With reference to FIG. 3, time-of-flight localization can also be used to identify lines-of-response that are not associated with the annihilation point of the positron. In such a case, the line-of-response is likely to be noise, and once identified can be advantageously discarded. In FIG. 3, a line-of-response LOR-X is acquired, which is sourced by an electron-positron annihilation event S-X occurring in the preclinical subject corresponding to the container region 40a. However, one of the two oppositely directed 511 keV gamma rays is scattered at a scattering site X. Accordingly, the acquired line-of-response LOR-X erroneously does not pass through the container region 40a, much less through the point of the electron-positron annihilation event S-X. Rather, the acquired line-of-response LOR-X erroneously passes through the container region 40d, so that considering the acquired line-of-response LOR-X without the time-of-flight localization information one might erroneously conclude that the acquired line-of-response LOR-X was sourced in the preclinical subject corresponding to the container region 40d.

However, by additionally considering time-of-flight localization information TOF-X, again represented in FIG. 3 by a Gaussian distribution plotted against the line-of-response LOR-X, it becomes apparent that it is highly unlikely that the acquired line-of-response LOR-X originated in the container region 40d. Moreover, because the acquired line-of-response LOR-X does not pass through any of the other container regions 40a, 40b, 40c, it can be concluded that the acquired line-of-response LOR-X is noise or otherwise represents erroneous data, and is not probative of any of the preclinical subjects, and accordingly can be discarded.

Figure 4:
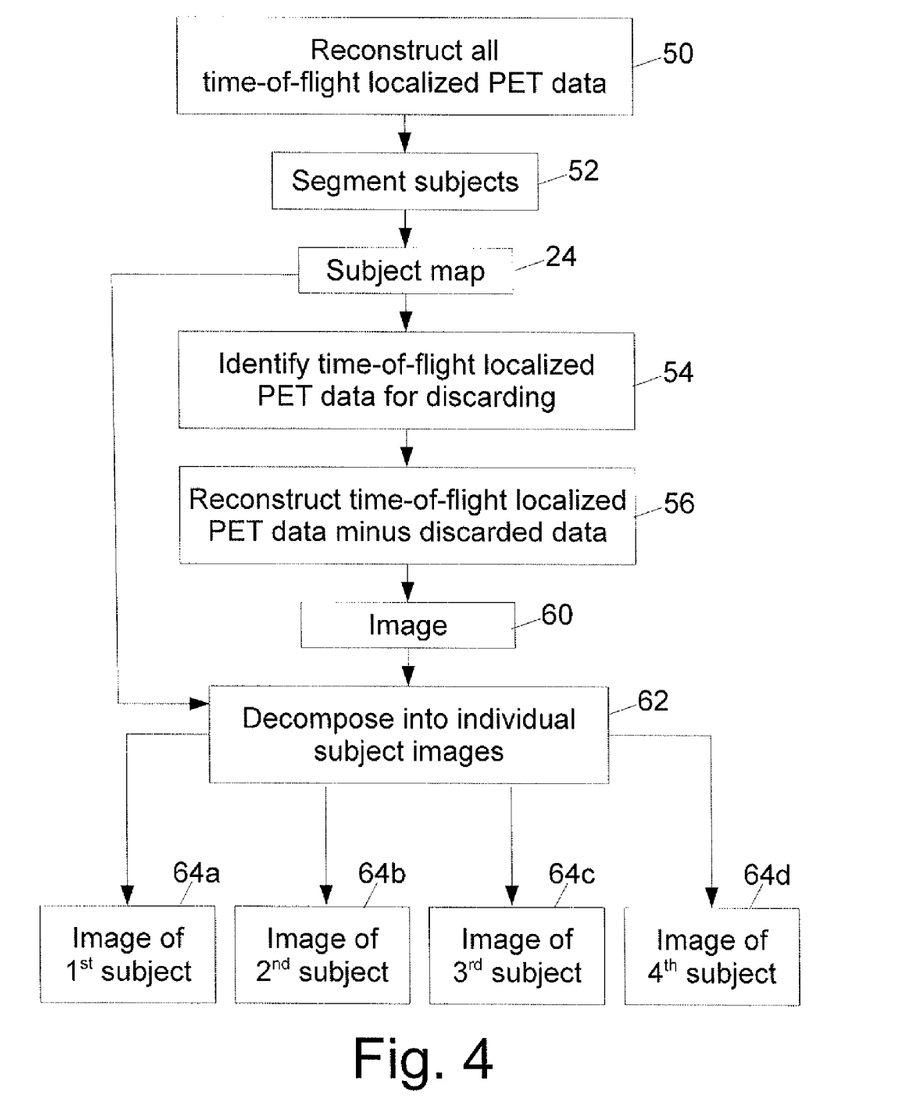
FIGS. 4-6 diagrammatically show illustrative preclinical imaging processes optionally performed using the preclinical imaging system of FIG. 1.

With reference to FIG. 4, an illustrative imaging process suitably practiced using the PET imaging system of FIG. 1 is described. The approach of FIG. 4 uses a two-pass reconstruction in which a first reconstruction pass 50 is segmented in an image segmentation operation 52 to generate the subject map 24. The first reconstruction pass 50 can employ substantially any reconstruction algorithm, and in some embodiments does not take into account time-of-flight localization information, although it is also contemplated to employ a reconstruction algorithm that takes into account time-of-flight localization along the lines-of-response. The segmentation operation 52 can employ any suitable segmentation algorithm, such as a thresholding algorithm, optionally followed by a grouping or clustering operation to identify contiguous regions. Moreover, in some embodiments the operations 50, 52 are omitted and the subject map 24 is obtained in another way, such as constructing the subject map 24 as a combination of container regions corresponding to known locations of preclinical subjects.

With continuing reference to FIG. 4, in a filtering operation 54 any time-of-flight localized PET data that are identified as noise are discarded. The filtering operation 54 suitably employs processing such as that already described with reference to FIG. 3. For example, a time-of-flight localized portion of each line-of-response can be identified as the segment portion of the line-of-response delineated by a full-width-at-half-maximum (FWHM) or other width measure of the time-of-flight distribution. If this segment portion does not intersect any of the preclinical subjects as indicated by the subject map 24, then the line-of-response is assumed to be noise and is suitably discarded.

In a second pass reconstruction 56, the time-of-flight localized PET data are again reconstructed, but this time minus any discarded lines-of-response that are removed by the filtering operation 54. As with the optional first pass reconstruction 50, the second pass reconstruction 56 can employ either a reconstruction algorithm that does not incorporate the time-of-flight localization information, or can employ a reconstruction algorithm that does incorporate the time-of-flight localization information. In some embodiments, the first pass reconstruction 50 does not incorporate the time-of-flight localization information since it is only intended to identify regions occupied by preclinical subjects and hence can be a low-resolution image, while the second pass reconstruction 56 does incorporate the time-of-flight localization information so as to provide enhanced image resolution. In either case, the second pass reconstruction 56 generates an image 60 that is suitably decomposed or segmented in a decomposition operation 62 into individual subject images 64a, 64b, 64c, 64d. The decomposition operation 62 advantageously optionally takes advantage of the subject map 24. For example, with reference back to the illustrative subject maps 24 of FIGS. 2 and 3, the container regions 40a, 40b, 40c, 40d optionally define corresponding individual subject images 64a, 64b, 64c, 64d. The individual subject images 64a, 64b, 64c, 64d are then suitably processed by the assessment electronics 30 of FIG. 1 to extract relevant information for each corresponding preclinical subject, such as tumor size, quantitative metastatic cancer information, or so forth.

In the processing of FIG. 4, both the optional first pass reconstruction 50 and the second pass reconstruction 56 process the set of PET data as a unit to generate a combined image that is then decomposed into individual preclinical subject images. The time-of-flight localization information are used to discard lines-of-response that are identified as noise, but are not used to positively associated lines-of-response with specific corresponding preclinical subjects.

Figure 5:
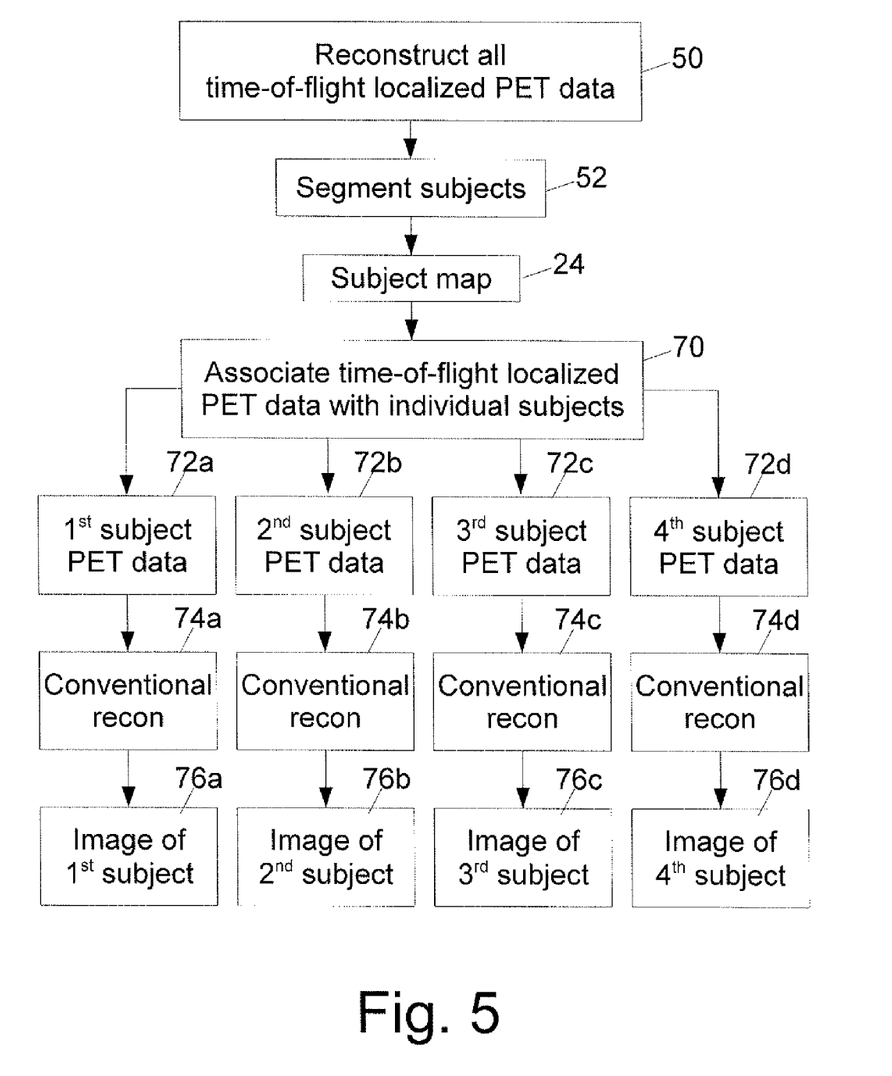

With reference to FIG. 5, in an alternative approach a data association operation 70 positively associates lines-of-response with specific preclinical subjects, reference the subject map 24, using an approach such as that already described with reference to FIG. 2. For example, a time-of-flight localized portion of each line-of-response can be identified as the segment portion of the line-of-response delineated by a full-width-at-half-maximum (FWHM) or other width measure of the time-of-flight distribution. If this segment portion intersects one of the preclinical subjects as indicated by the subject map 24, then the line-of-response is associated with that preclinical subject. If the segment portion does not intersect any of the preclinical subjects as indicated by the subject map 24, then the line-of-response is discarded. The result of this data association operation 70 are a set of PET data corresponding to each preclinical subject. For the illustrative example including four simultaneously imaged PET subject, the result of the operation 70 are four PET data sets 72a, 72b, 72c, 72d corresponding to the illustrative four simultaneously imaged preclinical subjects.

Each of the four PET data sets 72a, 72b, 72c, 72d are separately reconstructed in separate reconstruction operations 74a, 74b, 74c, 74d. The four separate reconstruction operations 74a, 74b, 74c, 74d can be performed serially by the same reconstruction pipeline, or in parallel or concurrently by four separate reconstruction pipelines. The serial approach implicates less hardware but is relatively slower, while the parallel approach implicates fourfold duplication of hardware but is relatively faster. Because each of the four PET data sets 72a, 72b, 72c, 72d has already taken into account the time-of-flight localization information by virtue of its segregation as a single distinct data set, the four separate reconstruction operations 74a, 74b, 74c, 74d in some embodiments employ a conventional PET reconstruction algorithm that ignores the time-of-flight information. Alternatively, the four separate reconstruction operations 74a, 74b, 74c, 74d can incorporate time-of-flight information, this latter approach being useful if the time-of-flight localization resolution is smaller than the typical size of the preclinical subject. In either approach, the result is four separate images 76a, 76b, 76c, 76d corresponding to the four preclinical subjects that were imaged simultaneously.

The approach of FIG. 5 can be advantageous over the approach of FIG. 4 because the separation of data from the different preclinical subjects is performed prior to reconstruction (or prior to the second-pass reconstruction in the case of a two-pass approach). By separating the data prior to reconstruction, the possibility that the reconstruction algorithm will introduce cross-talk in which data from one preclinical subject influences the reconstruction of another preclinical subject is reduced. Moreover, the reconstruction of smaller data sets can be faster, especially if parallel reconstruction pipelines are used to reconstruct the plurality of data sets concurrently.

In the approaches of FIGS. 4 and 5, it has been assumed that it is desired to reconstruct images of all preclinical subjects that are simultaneously imaged. However, in some circumstances the imaging may be intended for only one of the preclinical subjects, or may be intended for only a sub-group of the simultaneously imaged preclinical subjects. For example, the study may call for administering a contrast agent bolus to each subject and monitoring influx of the contrast agent. In such a circumstance, one may advantageously administer the bolus to a first preclinical subject and monitor the influx, followed by a repetition of this process on a second preclinical subject, and so forth. Because the contrast agent influx is a time-critical process, it can be advantageous to image only a single subject at a time. However, to enhance throughput, it may be advantageous to load several preclinical subjects at a time into the PET scanner 10.

Figure 6:
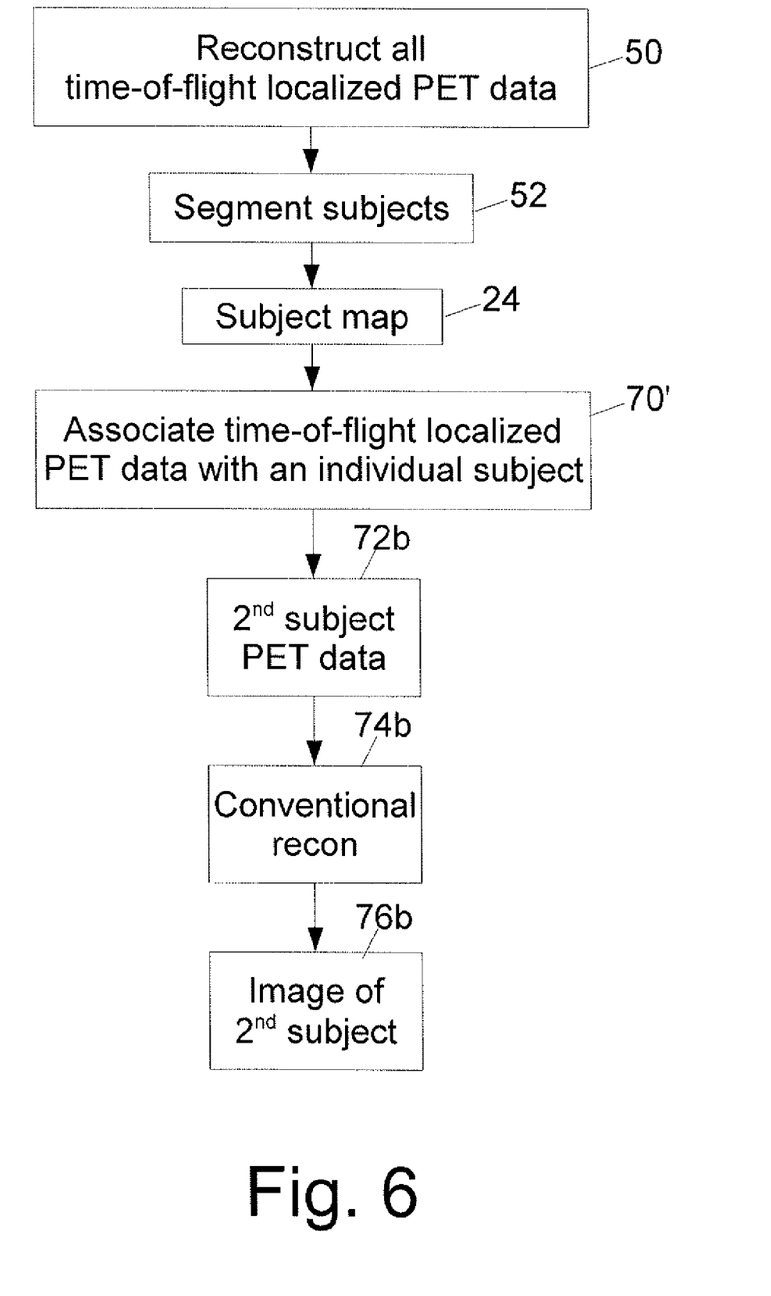

With reference to FIG. 6, the approach of FIG. 5 is modified to perform such an imaging sequence focusing on a single preclinical subject at a time. The process of FIG. 5 is modified in that a modified association operation 70' associates time-of-flight localized PET data with only the preclinical subject of interest, and discards any other time-of-flight localized PET data, so as to generate a single time-of-flight localized PET data set associated with a single selected preclinical subject. In FIG. 2, the selected preclinical subject is the second preclinical subject, although any other preclinical subject could be the selected subject. From this point the processing is the same as in FIG. 5 except that only the reconstruction operation 74b is performed to generate only the single image 76b. By limiting the association operation 70' to a single preclinical subject, and then reconstructing only the single data set 72b corresponding to that single preclinical subject, substantial processing speed is gained which can be useful for time-critical operations such as monitoring influx of a bolus.

In the foregoing, time-of-flight localization information has been described as used to associate PET data with particular subjects of a plurality of simultaneously imaged preclinical subjects, and/or to discard PET data that is not associated with any of the simultaneously imaged preclinical subjects. This use of the time-of-flight localization information is advantageous when the time-of-flight localization is small enough to assist in distinguishing which preclinical subject was the source of which lines-of-response. If the time-of-flight localization is smaller than an individual subject size, then optionally time-of-flight information may advantageously be used in the image reconstruction, either with or without performing data filtering or association based on the time-of-flight information. Thus, for example, if the time-of-flight localization is smaller than the preclinical subject size, then optionally the acquired PET data are reconstructed without pre-processing to discard or associate PET data, with the time-of-flight localization information being utilized by the reconstruction algorithm to improve signal-to-noise ratio or other characteristics of the reconstructed image. Moreover, the combination of time-of-flight localization that is smaller than the subject size with filtering to suppress noise as described with reference to FIG. 3 is an advantageous combination.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A preclinical positron emission tomography (PET) scanner comprising:

radiation detectors arranged to view an examination region;
coincidence electronics configured to acquire time-of-flight localized PET imaging data using the radiation detectors;
reconstruction electronics configured to reconstruct the time-of-flight localized PET imaging data to form an image representative of a distribution of a radiopharmaceutical in a plurality of preclinical subjects disposed in the examination region; and
a map of the plurality of preclinical subjects in the examination region;
the reconstruction electronics being configured to:
  (1) associate the time-of-flight localized PET imaging data with individual preclinical subjects based on the map of the plurality of preclinical subjects in the examination region to generate a set of time-of-flight localized PET imaging data for each preclinical subject, and
  (2) separately reconstruct each set of time-of-flight localized PET imaging data to generate images corresponding to the preclinical subjects.

2. The preclinical PET scanner as set forth in claim 1, wherein the time-of-flight localization is comparable to or larger than a size of the preclinical subjects.

3. The preclinical PET scanner as set forth in claim 1, wherein the preclinical subjects are rodents or rabbits.

4. The preclinical PET scanner as set forth in claim 1, the reconstruction electronics being further configured to discard time-of-flight localized PET imaging data indicated by the map as not probative of any of the preclinical subjects.

5. The preclinical PET scanner as set forth in claim 1, further comprising:
pre-clinical assessment electronics configured to generate a metastatic cancer measure based on the image.

6. The preclinical PET scanner as set forth in claim 5, wherein the pre-clinical assessment electronics are configured to classify pixels or voxels of the image as one of cancerous or non-cancerous and to generate the metastatic cancer measure based at least on a count or spatial distribution of the cancerous pixels or voxels.

7. A preclinical positron emission tomography (PET) imaging method comprising:
acquiring time-of-flight localized PET imaging data from a plurality of non-human subjects that have been administered a radiopharmaceutical; and
reconstructing the acquired time-of-flight localized PET imaging data to form an image representative of a distribution of radiopharmaceutical in a selected one or more of the non-human animal subjects, wherein the reconstructing comprises:
  identifying a sub-set of the time-of-flight localized PET imaging data associated with each of the selected one or more of the plurality of non-human animal subjects;
  discarding a portion of the time-of-flight localized PET imaging data identified based at least in part on time-of-flight localization information as not probative of the selected one or more of the plurality of non-human animal subjects; and
  reconstructing the acquired time-of-flight localized PET imaging data minus the discarded portion including reconstructing each sub-set to form an image representative of the distribution of radiopharmaceutical in the associated non-human animal subject.

8. The preclinical positron emission tomography (PET) imaging method as set forth in claim 7, wherein the reconstructing of the acquired time-of-flight localized PET imaging data minus the discarded portion does not utilize the time-of-flight localization information.

9. The preclinical positron emission tomography (PET) imaging method as set forth in claim 7, wherein the selected one or more of the plurality of non-human animal subjects include the entire plurality of non-human animal subjects.

10. The preclinical positron emission tomography (PET) imaging method as set forth in claim 7, further comprising:
   generating a metastatic cancer measure based on the image for each of the selected one or more of the non-human animal subjects.

11. A preclinical positron emission tomography (PET) scanner comprising:
   radiation detectors arranged to view an examination region;
   a subject support assembly configured to support a plurality of preclinical subjects in the examination region for simultaneous PET imaging;
   coincidence electronics configured to acquire time-of-flight localized PET imaging data from the plurality of preclinical subjects using the radiation detectors; and
   reconstruction electronics configured to (i) perform a filtering operation based at least in part on the time-of-flight information, the filtering operation including associating time-of-flight localized PET imaging data with individual preclinical subjects of the plurality of preclinical subjects to identify a sub-set of the time-of-flight localized PET imaging data associated with each preclinical subject of the plurality of preclinical subjects; and (ii) separately reconstruct each sub-set of the filtered time-of-flight localized PET imaging data to form images representative of radiopharmaceutical distribution in the plurality of preclinical subjects.

12. The preclinical positron emission tomography (PET) scanner as set forth in claim 11, wherein the reconstruction electronics reconstruct the filtered time-of-flight localized PET imaging data to form the images representative of radiopharmaceutical distribution in the plurality of preclinical subjects using a reconstruction algorithm that does not utilize the time-of-flight information.

13. The preclinical PET scanner as set forth in claim 1, wherein the reconstruction electronics are configured to separately reconstruct each set of time-of-flight localized PET imaging data to generate the images corresponding to the preclinical subjects without utilizing the time-of-flight localization information.

* * * * *